United States Patent
Fukuda et al.

(10) Patent No.: US 9,447,432 B2
(45) Date of Patent: Sep. 20, 2016

(54) METHOD FOR PRODUCING INDUCED PLURIPOTENT STEM CELLS

(75) Inventors: Keiichi Fukuda, Tokyo (JP); Shinsuke Yuasa, Tokyo (JP); Tomohisa Seki, Tokyo (JP); Mamoru Hasegawa, Tsukuba (JP)

(73) Assignees: Keio University, Tokyo (JP); DNAVEC Corporation, Ibaraki (JP)

( * ) Notice: Subject to any disclaimer, the term of this patent is extended or adjusted under 35 U.S.C. 154(b) by 0 days.

(21) Appl. No.: 13/641,370

(22) PCT Filed: Apr. 15, 2011

(86) PCT No.: PCT/JP2011/059429
§ 371 (c)(1),
(2), (4) Date: Apr. 10, 2013

(87) PCT Pub. No.: WO2011/129446
PCT Pub. Date: Oct. 20, 2011

(65) Prior Publication Data
US 2013/0189786 A1  Jul. 25, 2013

(30) Foreign Application Priority Data
Apr. 16, 2010  (JP) ................... 2010-095404

(51) Int. Cl.
*C12N 15/86* (2006.01)
*C12N 5/074* (2010.01)

(52) U.S. Cl.
CPC ............. *C12N 15/86* (2013.01); *C12N 5/0696* (2013.01); *C12N 2501/2302* (2013.01); *C12N 2501/515* (2013.01); *C12N 2501/602* (2013.01); *C12N 2501/603* (2013.01); *C12N 2501/604* (2013.01); *C12N 2501/606* (2013.01); *C12N 2502/13* (2013.01); *C12N 2506/11* (2013.01); *C12N 2510/00* (2013.01)

(58) Field of Classification Search
CPC ................ C12N 15/86; C12N 5/0696; C12N 2501/2302; C12N 2501/515; C12N 2501/602; C12N 2501/603; C12N 2501/604; C12N 2501/606; C12N 2502/13; C12N 2506/11; C12N 2510/00
See application file for complete search history.

(56) References Cited

U.S. PATENT DOCUMENTS

| | | |
|---|---|---|
| 2002/0169306 A1 | 11/2002 | Kitazato et al. |
| 2003/0022376 A1 | 1/2003 | Kitazato et al. |
| 2009/0068742 A1 | 3/2009 | Yamanaka |
| 2011/0223669 A1* | 9/2011 | Yamanaka ........... C12N 5/0696 435/455 |
| 2011/0236362 A1 | 9/2011 | Watarai et al. |
| 2011/0287538 A1 | 11/2011 | Fusaki et al. |
| 2012/0135525 A1 | 5/2012 | Brown et al. |

FOREIGN PATENT DOCUMENTS

| | | |
|---|---|---|
| EP | 1179594 A1 | 2/2002 |
| EP | 1186667 A1 | 3/2002 |
| EP | 2434012 A1 | 3/2012 |
| WO | WO-00/70055 A1 | 11/2000 |
| WO | WO-00/70070 A1 | 11/2000 |
| WO | WO 2007/069666 A1 | 6/2007 |
| WO | WO 2009/148057 A1 | 12/2009 |
| WO | WO-2009/157593 A1 | 12/2009 |
| WO | WO-2010/008054 A1 | 1/2010 |
| WO | WO-2010/027094 A1 | 3/2010 |
| WO | WO 2010/131747 A1 | 11/2010 |
| WO | WO-2010/134526 A1 | 11/2010 |
| WO | WO-2010/141801 A2 | 12/2010 |

OTHER PUBLICATIONS

Miyamoto. Biology of Reproduction, 80: 935-943, 2009.*
Wade et al. Eur. J. Biochem., 269:2284-2287, 2002.*
Gurdon & Colman. Nature, 402:743-746, 1999.*
Takahashi et al., Cell, 126: 663-676, 2006.*
Stadtfeld. Science, 322: 945-949, 2008.*
Okita. Science, 322: 949-953, 2008.*
Gonzalez. PNAS, 106(22): 8918-8922, 2009.*
Strelchenko, Embryonic Stem Cells for Morula in Methods in Enzymology, vol. 418, 2006, Lanza et al eds. 93-108.*
Stojovic, Reproduction, 2004, 128:259-267.*
Xu, Nature Biotech, 2002, 20:1261-1264.*
Bentin et al., Eur. J. Immunol, 18:627-632, 1988.*
Loh et al., Blood, 113(22): 5476-5479, Supplemental materials only, pp. 1-7.*
Aoi et al., "Generation of pluripotent stem cells from adult mouse liver and stomach cells," Science. 321(5889):699-702 (2008).
Brown et al., "Derivation of induced pluripotent stem cells from human peripheral blood T lymphocytes," PLoS One. 5(6):e11373 (2010).
Eminli et al., "Differentiation stage determines potential of hematopoietic cells for reprogramming into induced pluripotent stem cells," Nat Genet. 41(9):968-76 (2009).
Author manuscript of Hong et al., "Suppression of induced pluripotent stem cell generation by the p53-p21 pathway," available in PMC Aug. 6, 2010, published in final edited form as: Nature. 460(7259):1132-5 (2009). (13 pages).
Li et al. "A cytoplasmic RNA vector derived from nontransmissible Sendai virus with efficient gene transfer and expression," J Virol. 74(14):6564-9 (2000).
Riekstina et al., "Embryonic stem cell marker expression pattern in human mesenchymal stem cells derived from bone marrow, adipose tissue, heart and dermis," Stem Cell Rev. 5(4):378-86 (2009).
Takahashi et al., "Induction of pluripotent stem cells from adult human fibroblasts by defined factors," Cell. 131(5):861-72 (2007).

(Continued)

*Primary Examiner* — Thaian N Ton
(74) *Attorney, Agent, or Firm* — Clark & Elbing LLP (57) ABSTRACT

An object of the present invention is to provide methods for producing iPS cells with low invasivity and high efficiency. The iPS cells can be produced with high efficiency using a method comprising the steps of culturing mononuclear cells derived from peripheral blood for 3 to 14 days in the presence of anti-CD3 antibody, and subjecting the cultured mononuclear cells to dedifferentiation.

4 Claims, 6 Drawing Sheets

(56) References Cited

OTHER PUBLICATIONS

Takahashi et al., "Induction of pluripotent stem cells from fibroblast cultures," Nat Protoc. 2(12):3081-9 (2007).

Takahashi et al., "Induction of pluripotent stem cells from mouse embryonic and adult fibroblast cultures by defined factors," *Cell.* 126(4):663-76 (2006).

Anderson et al., "Anti-CD3+Interleukin-2 stimulation of marrow and blood: Comparison of proliferation and cytotoxicity," *Blood* 80: 1846-1853 (1992).

Fusaki et al., "Efficient induction of transgene-free human pluripotent stem cells using a vector based on Sendai virus, an RNA virus that does not integrate into the host genome," *Proc. Jpn. Acad. Ser. B* 85: 348-362 (2009).

Giorgetti et al., "Generation of induced pluripotent stem cells from human cord blood using *OCT4* and *SOX2*," *Cell Stem Cell* 5: 353-357 (2009).

Haase et al., "Generation of induced pluripotent stem cells from human cord blood," *Cell Stem Cell* 5: 434-441 (2009).

Hanna et al., "Direct reprogramming of terminally differentiated mature B lymphocytes to pluripotency," *Cell* 133: 250-264 (2008).

Loh et al., "Generation of induced pluripotent stem cells from human blood," *Blood* 113: 5476-5479 (2009).

Seki et al., "Generation of induced pluripotent stem cells from human terminally differentiated circulating T cells," *Cell Stem Cell* 7: 11-14 (2010).

Ye et al., "Human-induced pluripotent stem cells from blood cells of healthy donors and patients with acquired blood disorders," *Blood* 114: 5473-5480 (2009).

\* cited by examiner

SEQUENCE LISTING

```
<160> NUMBER OF SEQ ID NOS: 20

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
cagccccgat tcttccacca gtccc                                              25

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
cggaagattc ccagtcgggt tcacc                                              25

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
gacaggggga ggggaggagc tagg                                               24

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
cttccctcca accagttgcc ccaaac                                             26
```

-continued

```
<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
gggaaatggg aggggtgcaa aagagg                                              26

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
ttgcgtgagt gtggatggga ttggtg                                              26

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
acgatcgtgg ccccggaaaa ggacc                                               25

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
tgattgtagt gctttctggc tgggctcc                                            28

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
gcgtcctggg aagggagatc cggagc                                              26

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
ttgaggggca tcgtcgcggg aggctg                                              26

<210> SEQ ID NO 11
<211> LENGTH: 24
<212> TYPE: DNA
<213> ORGANISM: Artificial Sequence
<220> FEATURE:
<223> OTHER INFORMATION: Primer
```

<400> SEQUENCE: 11
cttatgctac gtaaaggagc tggg					24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
gtgccaaccc aggtcccgga agtt					24

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
cagatcctaa acagctcgca gaat					24

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
gcgtacgcaa attaaagtcc aga					23

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ggagccgcct gccctggaaa attc					24

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16 ttttcctga tattctattc ccat					24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ccgtccccgc aatctccttc catc					24

<210> SEQ ID NO 18
<211> LENGTH: 24

```
<212> TYPE: DNA
<213> ORGANISM: Artificial Sequence
<220> FEATURE:
<223> OTHER INFORMATION: Primer

<400> SEQUENCE: 18
atgatgccaa catggctccc ggtg                                           24

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
cagaacatca tccctgcctc tag                                            23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
ttgaagtcag aggagaccac ctg                                            23
```

METHOD FOR PRODUCING INDUCED PLURIPOTENT STEM CELLS

CROSS-REFERENCE TO RELATED APPLICATIONS

This application is the U.S. National Stage of the International Patent Application No. PCT/JP2011/059429, filed Apr. 15, 2011, which claims the benefit of Japanese Patent Application No. 2010-095404, filed Apr. 16, 2010.

TECHNICAL FIELD

The present invention relates to a method for producing induced pluripotent stem cells.

BACKGROUND ART

Induced pluripotent stem cells (iPS cells) would be useful for transplantation therapies for various diseases and are expected to be applied to regenerative medicine. It has been reported in recent years that iPS cells can be generated by selecting cells expressing Fbx15 gene from somatic cells such as fibroblasts and hepatocytes in which Oct3/4 gene, Sox2 gene, Klf4 gene, and c-Myc gene have been introduced and expressed (see, e.g., WO 2007/069666; Takahashi K, Yamanaka S. (2006). "Induction of pluripotent stem cells from mouse embryonic and adult fibroblast cultures by defined factors". Cell 126: 663-676; Takahashi K, Okita K, Nakagawa M, Yamanaka S. (2007). "Induction of pluripotent stem cells from fibroblast cultures". Nature Protocols 2: 3081-3089; Aoi T, Yae K, Nakagawa M, Ichisaka T, Okita K, Takahashi K, Chiba T, Yamanaka S. (2008). "Generation of pluripotent stem cells from adult mouse liver and stomach cells". Science 321(5889): 699-702).

DISCLOSURE OF THE INVENTION

Conventional methods of generating iPS cells, however, impose significant burdens on patients because of the necessity of obtaining tissue by a skin or liver biopsy, and have low efficiency of generating iPS cells. Therefore, an object of the present invention is to provide a method for producing iPS cells with low invasivity and high efficiency.

A method for producing induced pluripotent stem cells (iPS cells) according to the present invention uses mononuclear cells derived from peripheral blood as a starting material.

It is preferable that the aforementioned method for producing iPS cells comprises the steps of (i) culturing the mononuclear cells derived from peripheral blood for 3 to 14 days in the presence of anti-CD3 antibody and interleukin 2; and (ii) dedifferentiating the cultured mononuclear cells.

In addition, it is preferable that a dedifferentiation factor is introduced into said mononuclear cells in the step (ii). A recombinant expression vector that expresses said dedifferentiation factor may be introduced during the introduction of said dedifferentiation factor.

It is preferable that the dedifferentiation factors are Sox2, Oct3/4, Klf4 and c-Myc. It is more preferable that the recombinant expression vector is a Sendai virus vector.

It is preferable that the method for producing iPS cells according to the present invention further comprises the step of (iii) culturing the dedifferentiated mononuclear cells for 14 to 25 days in the presence of a growth factor. It is preferable that the peripheral blood is derived from human.

It should be noted that names of factors denoted in this specification without any word of "gene" or "cDNA", such as "Sox2", "Oct3/4", "Klf4", and "c-Myc" represent proteins, i.e., gene products of these genes.

MODE FOR CARRYING OUT THE INVENTION

Embodiments of the present invention that were completed based on the aforementioned findings are described in detail in reference to Examples.

Unless otherwise noted in embodiments and examples, all procedures used are as described in standard protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., with or without modifications or changes. In addition, unless otherwise noted, a commercial reagent kit or a measurement instrument, if any, is used as described according to protocols attached thereto.

The above and further objects, features, advantages, and ideas of the present invention are apparent to those skilled in the art from consideration of the detailed description of this specification. Furthermore, those skilled in the art can easily reproduce the present invention from these descriptions. The mode(s) and specific example(s) described below represent a preferable embodiment of the present invention, which is given for the purpose of illustration or description. The present invention is not limited thereto. It is obvious to those skilled in the art that various modifications may be made according to the descriptions of the present specification without departing from the spirit and scope of the present invention disclosed herein.

Hereinafter, methods for producing iPS cells using mononuclear cells derived from peripheral blood as a starting material are described in detail.

The peripheral blood is preferably derived from a mammal and may be derived from an animal such as a mouse, a rat, a hamster, a guinea pig, a rabbit, a sheep, a horse, a pig, a cat, a dog, and a monkey. It is more preferable that the peripheral blood is derived from a human. The animal may be at any stage of development including adult, young, fetus, and embryo. The stage of development is not limited as long as peripheral blood containing mononuclear cells can be obtained. While any conventional method of blood collection can be used that is appropriately selected by those skilled in the art in consideration of the size of the animal or the amount of blood to be collected, it is preferable to use a syringe in order to reduce the burden of the animal.

When the iPS cells produced using the method according to the present invention are used for treating a patient or a sick animal suffering from a certain disease, it is preferable that the peripheral blood is derived from an animal of the same species as the patient or the sick animal. It is more preferable that the peripheral blood is derived from the patient or the sick animal.

The mononuclear cells may be contaminated with other cells or components derived from the peripheral blood or may be composed of mononuclear cells only. It is, however, preferable that the concentration of the mononuclear cells is high in terms of efficiency of production of the iPS cells. The specific method to prepare mononuclear cells from peripheral blood can be appropriately selected by those skilled in the art. For example, density gradient centrifugation, Lympho-Kwik (One Lambda), or immunomagnetic beads may be used. In the density gradient centrifugation, any density medium appropriately selected by those skilled in the art can be used such as a sucrose solution, a Ficoll solution, an aqueous solution of a copolymer of sucrose and epichlorohydrin (e.g., Ficoll-Conray and Ficoll-Hypaque), or a solution of colloidal silica particles coated with polyvinyl pyrrolidone (e.g., Percoll). It is preferable that the peripheral blood used is freshly collected, but the one stored under refrigerated or frozen conditions may also be used.

==Culture of Mononuclear Cells Derived from Peripheral Blood==

Mononuclear cells prepared from peripheral blood are cultured for 3 to 14 days, preferably 3 to 7 days, in the presence of anti-CD3 antibody and interleukin. This culture procedure is expected to specifically promote the growth of CD3– positive T cells in the mononuclear cells.

Culture conditions can be appropriately selected by those skilled in the art. For example, mononuclear cells may be cultured at 35° C. to 40° C., preferably 37° C., in the presence of 5% $CO_2$. Culture medium can be appropriately selected by those skilled in the art from those commonly used for mononuclear cells. The culture medium may be, for example, KBM502, DMEM/F12, DMEM, KBM530, KBM540, KBM560, or RPM1640. It is preferable that the culture medium is KBM502.

The anti-CD3 antibody may be immobilized on a culture dish or a culture tube, or be suspended in a liquid culture medium. When the anti-CD3 antibody is immobilized, it may be immobilized on a plastic surface of the culture dish or the culture tube by, for example, covalent reaction or non-covalent binding such as electrostatic interaction. The immobilization method is not specifically limited and can be appropriately selected from methods known to those skilled in the art. Alternatively, culture dishes or culture tubes on which the anti-CD3 antibody is immobilized may be purchase from, for example, BD BioCoat. While those skilled in the art can determine the optimum concentration of the anti-CD3 antibody in the liquid culture medium, it is preferable that the concentration is within a range of 1 to 100 μg/ml in consideration of the yield of generated iPS cells. The anti-CD3 antibody is not limited as long as it can specifically stimulate CD3 antigen on mononuclear cells used as a starting material and enhance proliferation of CD3 antigen-positive mononuclear cells. The antibody may be polyclonal or monoclonal, and may be obtained from any animal. The antibody may be a part of antibody with the antigen binding site containing the variable region. It may be, for example, a Fab fragment or a $F(ab')_2$ fragment.

The interleukin may be any one of known interleukins. Examples include interleukin 1, interleukin 2, interleukin 4, interleukin 6, interleukin 8, interleukin 11, and interleukin 12. It is preferable to use a commercially available interleukin 2 from the viewpoint of handling and easiness of preparation.

In addition to the aforementioned antibodies and interleukins, the culture medium may contain one or more substances to be added to a culture of mononuclear cells. Examples of such substances include, but not limited to, growth factors such as a fibroblast growth factor (FGF) and an epidermal growth factor (EGF), FBS and knockout serum replacement (Invitrogen), L-glutamine, non-essential amino acids, antibiotics such as penicillin and streptomycin, and mercaptoethanol.

==Dedifferentiation of Mononuclear Cells==

Next, the mononuclear cells are subjected to dedifferentiation.

Dedifferentiation of the mononuclear cells can be carried out using a method known to those skilled in the art. The method used is not limited as long as desired iPS cells can be generated. For example, a dedifferentiation factor may be used, or alternatively, a known agent that promotes dedifferentiation of mononuclear cells may be added. As the dedifferentiation factor, a dedifferentiation factor or factors commonly used in generating iPS cells (i.e. reprogramming factor(s)) can be used. Reprogramming methods described in, for example, the article by Takahashi et al. (Cell 2007 vol. 131: 861-872) can be used for dedifferentiation, whose disclosure is incorporated herein by reference. It is preferable that the dedifferentiation factors to be introduced comprise, in combination, products of genes selected from each of the Oct family, the Klf family, and the Sox family. It is also preferable that the dedifferentiation factors to be introduced comprise a product of a gene in the Myc family. Examples of Oct family genes include Oct 3/4, Oct1A, and Oct6. Examples of Klf family genes include Klf1, Klf2, Klf4, and Klf5. Examples of Sox family genes include Sox1, Sox2, Sox3, Sox7, Sox15, Sox17, and Sox18. Examples of Myc family genes include c-Myc, N-Myc, and L-Myc. In addition to the combination of these genes, a cytokine or a chemical compound may be applied to the culture medium as a supplemental factor.

Combinations of the dedifferentiation factors other than those described above include those comprising product(s) of, for example, Nanog gene and/or lin-28 gene in addition to products of a gene in the Oct family and a gene in the Sox family. In addition to the combinations of these dedifferentiation factors, product of SV40 Large T antigen gene, product of TERT gene, and/or an immortalizing factor may be used.

In cases where one or more of the aforementioned dedifferentiation factor(s) is/are expressed in the mononuclear cells to be dedifferentiated with the dedifferentiation factor(s), the dedifferentiation factor(s) is/are not required to be introduced. A chemical compound capable of providing a function of a certain dedifferentiation factor, if any, may be used in place of the dedifferentiation factor in question. For example, a cytokine or a chemical compound can substitute for a product of a Myc family gene. Examples of the cytokine for this purpose include SCF and bFGF. Valproic acid is an example that can substitute for a c-Myc gene or a Klf4 gene.

Genes encoding the dedifferentiation factors are highly conserved in vertebrate species and represent those including homologues unless the name of the animal is specifically mentioned. In addition, the dedifferentiation factors also include products encoded by genes with mutations including polymorphisms, as long as they have similar functions to those of products of the wild-type genes. Examples include products of mutated genes in which 1 to 10, preferably 1 to 6, more preferably 1 to 4, still more preferably 1 to 3, and even more preferably 1 to 2 amino acid(s) of the products of the wild-type genes is/are substituted, inserted, or deleted.

A method of dedifferentiating the mononuclear cells using the aforementioned dedifferentiation factor(s) is not specifically limited. For example, a dedifferentiation factor or factors may be introduced into mononuclear cells to achieve dedifferentiation. More specifically, a complex of a cationic lipid reagent such as SAINT-PhD (Cosmo Bio) or Cellvader (GE Healthcare) and a dedifferentiation factor, or a complex of a peptide that is referred to as a protein transduction domain (PTD) and a dedifferentiation factor is prepared. The complex is added to a culture medium for the mononuclear cells so that the complex is in contact with the cells, thereby introducing the dedifferentiation factor into the cells. The mononuclear cells after the introduction of the dedifferentiation factor(s) are dedifferentiated into a pluripotent state. The amount of the dedifferentiation factor(s) to be added can appropriately be determined by those skilled in the art.

Alternatively, an expression vector that is capable of expressing a dedifferentiation factor(s) may be introduced into the mononuclear cells to achieve the dedifferentiation of the mononuclear cells. For DNA vectors, a recombinant expression vector is prepared by introducing a gene encoding a dedifferentiation factor (dedifferentiation factor gene) into the downstream of an appropriate promoter for expression in the mononuclear cells. In negative-strand RNA viruses such as Sendai viruses, a dedifferentiation factor gene is expressed by using a promoter derived from the virus. For such an RNA vector derived from a virus, prepared is a recombinant virus vector having RNA that encodes a dedifferentiation factor in the genome. Two or more dedifferentiation factor genes may be inserted into a single vector. The expression vector to be used is not specifically limited as long as it has a desired function of inducing dedifferentiation. The expression vector may be a wild-type, mutant, natural, or artificially modified vector. It is preferable that the expression vector is a virus vector. The expression vector may be a virus vector derived from, for example, a Sendai virus, a retrovirus, an adenovirus, an adeno-associated virus, or a poxvirus. It is, however, the expression vector is preferably a vector derived from a Sendai virus that is characterized by not being integrated into the host chromosome.

It is preferable that such a Sendai virus vector has a gene encoding a protein required for genome replication, such as N protein, P protein, and L protein, in order to induce the dedifferentiation of the mononuclear cells. The artificially modified Sendai virus vector may have cytotoxic or thermosensitive mutations. For example, it may have a mutation or a deficiency in a gene encoding envelope protein or coat protein of the virus, such as F gene, H gene, HN gene, or G gene derived from a negative-strand RNA virus (see, WO 00/70055, WO 00/70070, Li, H. O. et al., J. Virol. 74(14) 6564-6569 (2000)). Such a Sendai virus vector is safer because it is able to replicate its genome but is not able to form infectious virus particles in mononuclear cells. It is particularly preferable to use an F gene-deleted Sendai virus vector.

The recombinant expression vector or the virus particle prepared as described above is introduced into the mononuclear cells. For this purpose, the recombinant expression vector such as a plasmid or the virus particle is added to the culture medium to introduce the gene of interest into the mononuclear cells. When the recombinant expression vector such as a plasmid is added, it can be introduced into the mononuclear cells by using a known method of gene introduction such as calcium phosphate transfection, lipofection, DEAE-dextran mediated transfection, and electroporation. When the virus particle such as a recombinant Sendai virus is added, the gene of interest is introduced into the mononuclear cells by infection of that virus to the mononuclear cells.

The dedifferentiation factor is expressed in the mononuclear cells carrying the recombinant expression vector, and the mononuclear cells are dedifferentiated with the expressed dedifferentiation factor. The amount of the recombinant expression vector to be added can appropriately be determined by those skilled in the art.

During the introduction of the dedifferentiation factor, the mononuclear cells are cultured in a serum-free medium for 1 to 5 days, preferably 2 days, at 35° C. to 40° C., preferably 37° C., in the presence of 5% $CO_2$. The serum-free medium may be DMEM/F12, VP-SFM, DMEM, KBM530, KBM540, KBM560, ROM1640, or KBM502, but preferably KBM502. In this culture, MEF (mouse embryonic fibroblast) feeder cells or SNL (mouse embryonic fibroblast cell line) feeder cells may be used.

==Culture after Dedifferentiation==

The mononuclear cells dedifferentiated as described above are cultured for 10 to 30 days, preferably 14 to 25 days, more preferably 20 days, under typical conditions for culturing the iPS cells. For example, they may be cultured using DMEM/F12 containing a growth factor at 35° C. to 40° C., preferably 37° C., in the presence of 5% $CO_2$. Alternatively a culture medium such as DMEM may be used. MEF feeder cells or SNL feeder cells may also be used. The growth factor to be used is not specifically limited and can appropriately be selected from well-known growth factors by those skilled in the art. It may be a fibroblast growth factor (FGF) or an epidermal growth factor (EGF).

In addition to the aforementioned growth factor, the medium may contain one or more substances that are commonly added to a culture of mononuclear cells. Examples of such substances include, but not limited to, serum such as FBS and knockout serum replacement (Invitrogen), L-glutamine, non-essential amino acids, antibiotics such as penicillin and streptomycin, and mercaptoethanol.

EXAMPLES

This Example shows that iPS cells can be produced efficiently from mononuclear cells derived from peripheral blood using a method for producing iPS cells according to the present invention. All cultures were performed under conditions at 37° C., in the presence of 5% $CO_2$.

==Preparation of Mononuclear Cell Fractions==

1 to 20 ml of peripheral blood was obtained from healthy volunteers (five male and female subjects, 11-66 years of age) who had given informed consent according to the protocol approved by the Ethical Committee of Keio University Hospital. From the peripheral blood, mononuclear cell fractions were isolated by Ficoll-Hypaque (GE Healthcare) gradient centrifugation (30 min, 400×g).

==Recombinant Sendai Virus Vector==

Sendai viruses were prepared using a known method (WO 2010/008054) by which each of the following (1) to (4) dedifferentiation factor genes was introduced into the SeV18+/TSΔF vector (WO 2010/008054):
 (1) Oct3/4 gene
 (2) Klf4 gene
 (3) c-Myc gene
 (4) Sox2 gene.

More specifically, the following plasmid vectors were introduced into 293T/17 cells: one plasmid vector which expresses a recombinant virus genome as cDNAs encoding a negative-strand RNA virus genome RNA (negative-strand) or a complementary strand thereof (positive-strand) containing either of the genes (1) to (4); and other plasmid vectors that express proteins (F, N, P, L, T7 RNA polymerase) required for self-replication of the virus. Then, LLC-MK2/F/A cells that express F protein were overlaid and cultured. The supernatants containing the produced virus were collected to produce the recombinant Sendai viruses.

==Preparation of Feeder Cells==
(Mouse Embryonic Fibroblast Cell Line, SNL)

First, 0.1% gelatin was added to dishes. The dishes were left at 37° C. for about 1 hour to be coated with the gelatin. SNL (EGACC) was adjusted to a density of $1.5 \times 10^5$ cells/ml. The cells were plated on the dishes (10 cm in diameter) in the amount of 10 ml per dish, and incubated overnight to prepare feeder cells.

==Culture of Mononuclear Cells Using Anti-CD3 Antibody==

Anti-CD3 antibody (BD Biosciences) was diluted in PBS to 10 µg/ml. The bottom of 6-well dishes was overlaid with this diluted antibody solution and the dishes were incubated at 37° C. for 30 minutes to 3 hours. The diluted antibody solution was discarded immediately before use, and the dishes were rinsed with PBS and used as the anti-CD3 antibody-coated dishes.

The mononuclear cells derived from peripheral blood were seeded at $1 \times 10^5$ to $1 \times 10^6$ cells/ml on the dishes coated with the anti-CD3 antibody and were incubated in 10 ml of KBM502 medium (containing 20 U/ml of recombinant interleukin 2) for 5 days.

==Dedifferentiation of Mononuclear Cells==
(First Day of Dedifferentiation)

The mononuclear cells cultured with the anti-CD3 antibody were adjusted to a density of $7.5 \times 10^5$ cells/ml, to which Sendai virus was added at MOI of 1, 3, 5, 10, or 20 to introduce a recombinant vector. Then, the cells were incubated in the KBM502 medium for 24 hours.

(Second Day of Dedifferentiation)

The cells in each well were harvested with a cell scraper, and the culture medium containing the cells was collected into a tube for each well. The tubes were centrifuged at 800 to 1000 rpm for 5 minutes at 20° C. Then, 2 ml of the KBM502 medium was added to the pellets, which were disrupted by pipetting several times to an extent that they are not broken down into single cells, and suspended. The suspensions were returned to the wells in the original dishes and were incubated in the KBM502 medium for 24 hours.

(Third Day of Differentiation)

The cells in each well were harvested with a cell scraper, and the culture medium containing the cells was collected into a tube for each well. The cells were pipetted into single cells, and the number of the cells was counted. The tubes were centrifuged at 800 to 1000 rpm for 5 minutes at 20° C. Then, an appropriate amount of KBM502 medium was added to the pellets. The pellets were pipetted into single cells. The mononuclear cells were seeded at $5 \times 10\%$ $5 \times 10'$, and $5 \times 10^6$ cells/dish on the feeder cells (SNL) prepared in the 10 cm dishes, and were incubated in the KBM502 medium for 24 hours.

==Culture after Dedifferentiation==

The cells treated for dedifferentiation as described above were seeded on the feeder cells (SNL), and the culture medium was replaced with an iPS cell medium (10 ml/10 cm dish) supplemented with 10 ng/ml human basic fibroblast growth factor (bFGF, Wako Pure Chemical Industries). Then, the culture medium was replaced every 48 hours to continue the culture for 20 days. It should be noted that the iPS cell medium was made up of DMEM/F12 (Invitrogen), 20% knockout serum replacement (Invitrogen), 2 mM L-glutamine (Invitrogen), $1 \times 10^{-4}$ M non-essential amino acids (Invitrogen), $1 \times 10^{-4}$ 2-mercaptoethanol (Invitrogen), and 0.50% penicillin-streptomycin (Wako Pure Chemical Industries).

==Alkaline Phosphatase Staining and Crystal Violet Staining==

Colonies obtained by the dedifferentiation induction were stained for alkaline phosphatase and with crystal violet. First, the colonies were fixed in 10% neutral buffered formalin solution (Wako Pure Chemical Industries) and were stained with 1-Step NBT/BCIP (Pierce). Furthermore, the crystal violet was dissolved in methanol to prepare a 4% crystal violet solution. This solution was added to the cells to stain the cells for 30 minutes. The alkaline phosphatase is known to be expressed in stem cells and is thus used as a marker for the stem cells (see, for example, Riekstina U. et al., Stem Cell Rev. 2009 December 5(4): 378-386); and the crystal violet only stained the living cells. After these stainings, DAPI (Molecular Probes) was used for nuclear counterstaining.

As shown in FIG. 1, 80 to 90% of the colonies of the living cells were alkaline phosphatase positive when the dedifferentiation induction was performed at any one of MOI 3 to 20.

==Analysis of Expression of Stem Cell Marker Proteins Using Immunohistochemical Staining==

Three colonies were randomly cloned from the colonies of the aforementioned alkaline phosphatase positive cells. DAPI staining and alkaline phosphatase staining as well as morphological observation were carried out to confirm that these cells were iPS cells. It was found that all of the three clones have typical morphological features of the embryonic stem cells or the iPS cells and were alkaline phosphatase positive.

Figure 1:
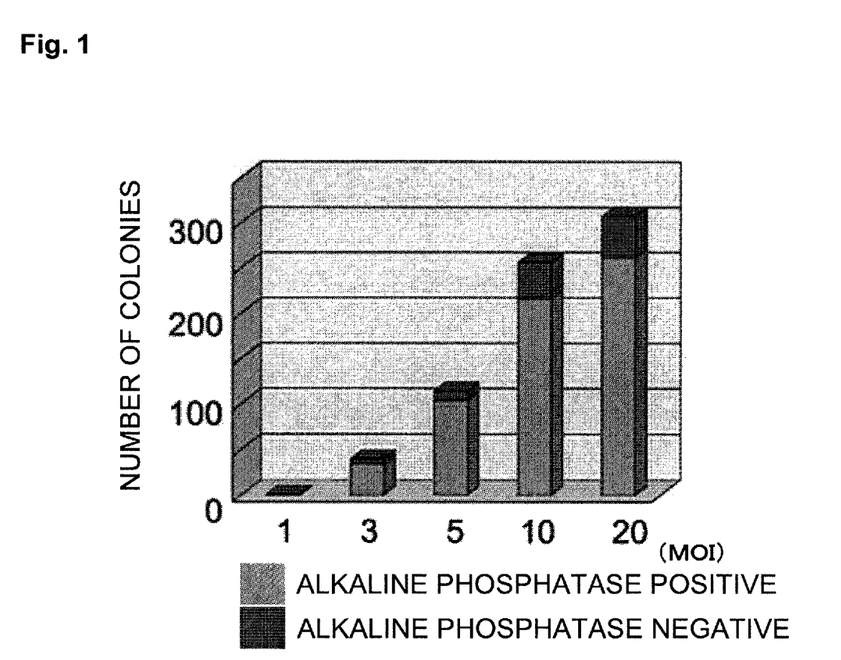
FIG. 1 shows a graph representing a ratio of colonies of alkaline phosphatase-positive stem cells, obtained by dedifferentiation of mononuclear cells with the addition of a virus at MOI 1 to 20 to a culture medium of the mononuclear cells cultured in the presence of CD3 antibody in one Example of the present invention.
Figure 2:
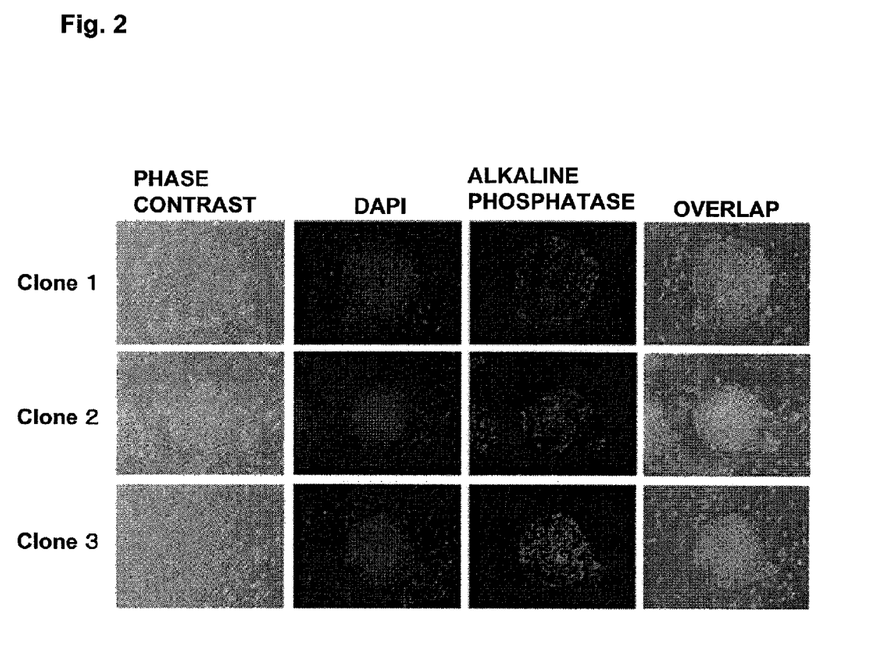
FIG. 2 shows micrographs of iPS cells, produced from mononuclear cells derived from peripheral blood, which were stained with alkaline-phosphatase and DAPI stainings in one Example of the present invention.
Figure 3:
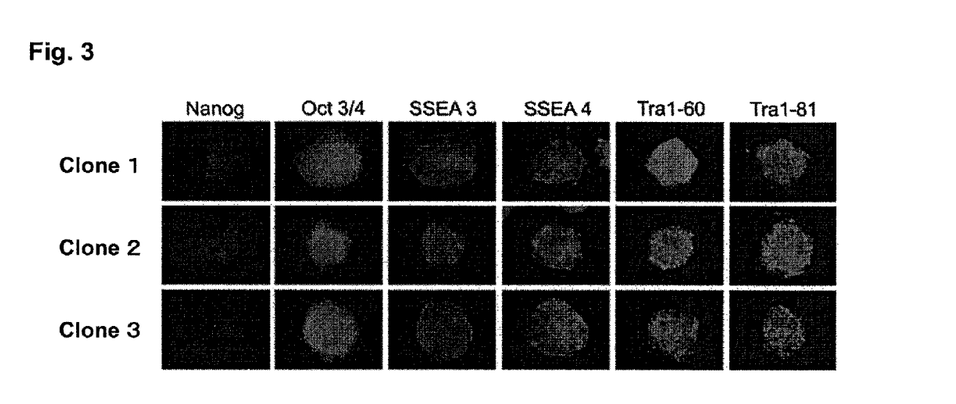
FIG. 3 shows photographs of immunohistochemical staining of stem cell marker proteins in the iPS cells produced from the mononuclear cells derived from peripheral blood in one Example of the present invention.

Next, colonies of clones obtained by the dedifferentiation induction were fixed in 10% neutral buffered formalin solution (Wako Pure Chemical Industries) and were reacted with anti-Nanog antibody (reproCELL, 1000-fold dilution), anti-Oct3/4 antibody (Santa Cruz, 100-fold dilution), anti-SSEA3 antibody (Millipore, 200-fold dilution), anti-SSEA4 antibody (Millipore, 200-fold dilution), anti-Tra160 antibody (Millipore, 200-fold dilution), and anti-Tra181 antibody (Millipore, 200-fold dilution). Subsequently, anti-rabbit IgG antibody, anti-mouse IgG antibody or anti-mouse IgM antibody (all of them were obtained from Molecular Probes) labeled with Alexa488 or Alexa568 was appropriately used as secondary antibody. Stained cells were examined under a fluorescence microscope (Olympus IX70), and the proteins were detected for all stem cell markers examined in all of the three clones, as shown in FIG. 3.

==Analysis of Gene Expression of Stem Cell Markers Using RT-PCR==

The cells of each clone were analyzed in terms of protein and gene expressions of these stem cell markers using immunohistological staining and reverse transcription polymerase chain reaction (RT-PCR). RT-PCR was also used for similar analyses of the mononuclear cells before and after dedifferentiation. Human embryonic stem cells (KhES-2, obtained from Kyoto University) were used as positive control cells.

Figure 4:
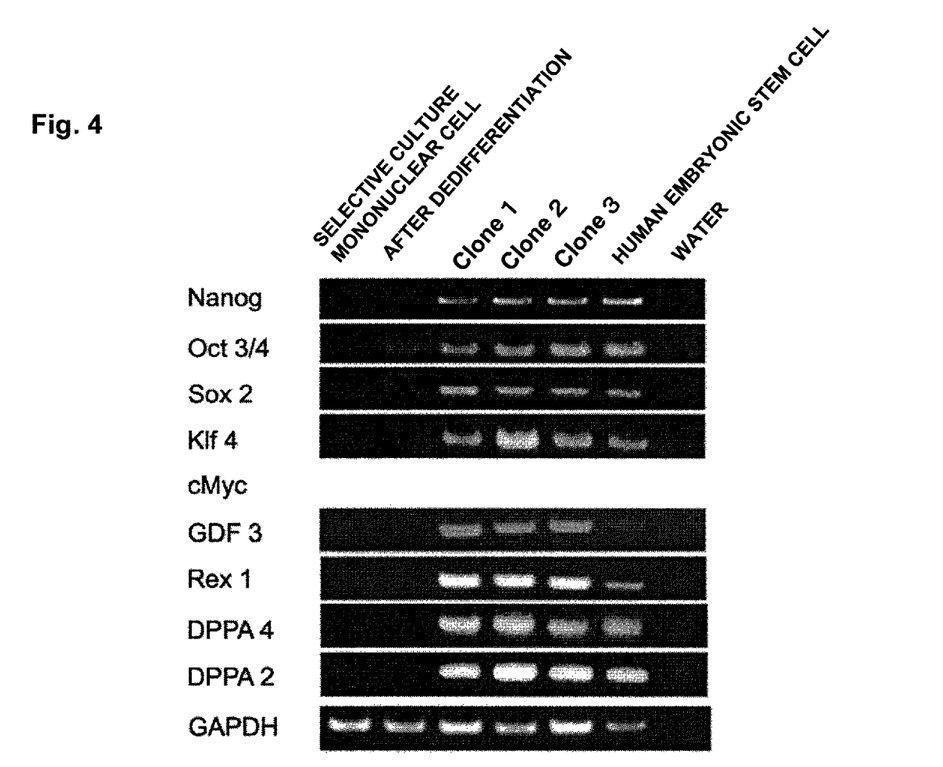
FIG. 4 shows expression of stem cell marker genes, analyzed by RT-PCR, in the iPS cells produced from the mononuclear cells derived from peripheral blood in one Example of the present invention.

Total RNA was isolated from the cells of each clone using TRIZOL (Invitrogen). Then, cDNA was prepared from this total RNA using Superscript First-Strand Synthesis System (Invitorgen). RT-PCR was performed with KOD plus (DNA polymerase, Toyobo) using the cDNA as template and the following primers. Gene expressions of the stem cell markers expressed in the human embryonic stem cells were detected in all of the three clones, as shown in FIG. 4.

```
Primers:
Nanog-F:
                                    (SEQ ID NO: 1)
CAGCCCCGATTCTTCCACCAGTCCC Nanog-R:
                                    (SEQ ID NO: 2)
CGGAAGATTCCCAGTCGGGTTCACC Oct 3/4-F:
                                    (SEQ ID NO: 3)
GACAGGGGGAGGGGAGGAGCTAGG Oct 3/4-R:
                                    (SEQ ID NO: 4)
CTTCCCTCCAACCAGTTGCCCCAAAC Sox 2-F:
                                    (SEQ ID NO: 5)
GGGAAATGGGAGGGGTGCAAAAGAGG Sox 2-R:
                                    (SEQ ID NO: 6)
TTGCGTGAGTGTGGATGGGATTGGTG Klf 4-F:
                                    (SEQ ID NO: 7)
ACGATCGTGGCCCCGGAAAAGGACC Klf 4-R:
                                    (SEQ ID NO: 8)
TGATTGTAGTGCTTTCTGGCTGGGCTCC cMyc-F:
                                    (SEQ ID NO: 9)
GCGTCCTGGGAAGGGAGATCCGGAGC cMyc-R:
                                    (SEQ ID NO: 10)
TTGAGGGGCATCGTCGCGGGAGGCTG GDF 3-F:
                                    (SEQ ID NO: 11)
CTTATGCTACGTAAAGGAGCTGGG GDF 3-R:
                                    (SEQ ID NO: 12)
GTGCCAACCCAGGTCCCGGAAGTT Rex 1-F:
                                    (SEQ ID NO: 13)
CAGATCCTAAACAGCTCGCAGAAT Rex 1-R:
                                    (SEQ ID NO: 14)
GCGTACGCAAATTAAAGTCCAGA DPPA 4-F:
                                    (SEQ ID NO: 15)
GGAGCCGCCTGCCCTGGAAAATTC DPPA 4-R:
                                    (SEQ ID NO: 16)
TTTTTCCTGATATTCTATTCCCAT DPPA 2-F:
                                    (SEQ ID NO: 17)
CCGTCCCCGCAATCTCCTTCCATC DPPA 2-R:
                                    (SEQ ID NO: 18)
ATGATGCCAACATGGCTCCCGGTG GAPDH-F:
                                    (SEQ ID NO: 19)
CAGAACATCATCCCTGCCTCTAG GAPDH-R:
                                    (SEQ ID NO: 20)
TTGAAGTCAGAGGAGACCACCTG
```

These results indicate that the cells generated in this Example are iPS cells.

As apparent from the above, iPS cells can be generated with high efficiency by culturing the mononuclear cells derived from peripheral blood in the presence of the anti-CD3 antibody without isolating the CD3 positive T cells from the mononuclear cells derived from peripheral blood using, for example, FACS, and then dedifferentiating the cells.

Comparative Example 1

In Comparative Examples, T cells are sorted by FACS from the mononuclear cell fraction derived from peripheral blood to produce iPS cells.

First, CD3 positive T cells were sorted by FACS from the same amount of the mononuclear cell fraction derived from peripheral blood as those used in the Example. After sorting, about 30 to 40% of cells in the mononuclear cell fraction derived from peripheral blood was obtained as the CD3-positive T cells. The sorted T cells were seeded on dishes coated with the anti-CD3 antibody, and were cultured in 10 ml of KBM502 medium containing recombinant interleukin 2 (20 U/ml) for 5 days.

The cultured T cells were adjusted to a density of $7.5 \times 10^5$ cells/ml. The recombinant Sendai virus was added to the cells as in the Example at MOI 3 or 20 to introduce the recombinant vector, thereby dedifferentiating the cells.

The cells in the colonies obtained by the dedifferentiation induction were stained with alkaline phosphatase or crystal violet.

Figure 5:
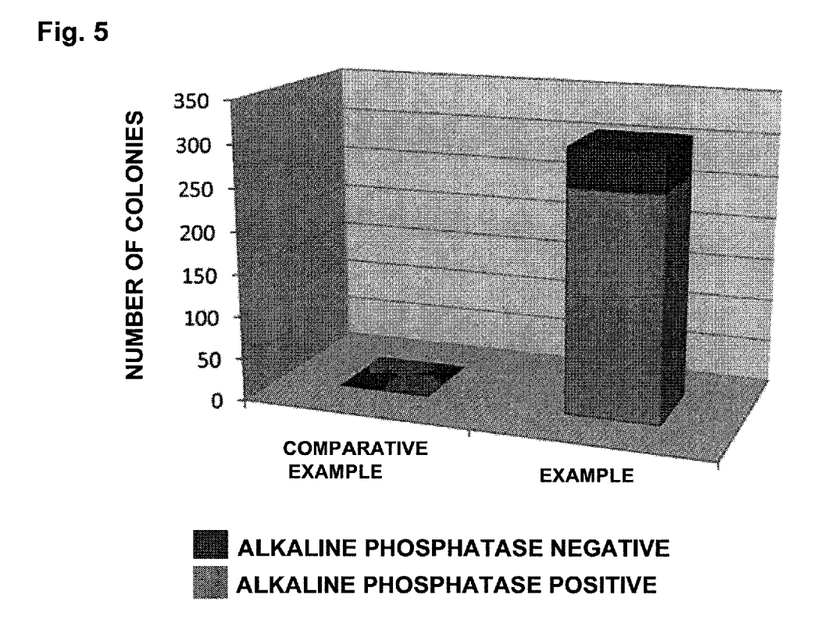
FIG. 5 shows a graph comparing the number of colonies of alkaline phosphatase-positive stem cells (Comparative Example), obtained by dedifferentiation of mononuclear cells with the addition of a virus at MOI 20 to T cells sorted by FACS with the number of colonies (Example) obtained by dedifferentiation at MOI 20 in the Example, in one Example of the present invention.

FIG. 5 shows a graph comparing the number of colonies obtained by the dedifferentiation induction at MOI 20 in this Comparative Example with the number of colonies obtained by the dedifferentiation induction at MOI 20 in the Example. Only few colonies were obtained in the Comparative Example even when alkaline phosphatase positive and negative colonies were both included.

Comparison between the Comparative Example and the Example indicated that the method in the Example is about 100 times higher in efficiency of establishing the iPS cells than the method in the Comparative Example.

Comparative Example 2

This Comparative Example shows that a step of culturing mononuclear cells in the presence of anti-CD3 antibody and interleukin 2 is required when the iPS cells are generated from the mononuclear cells described in the Example.

First, mononuclear cells obtained from peripheral blood were seeded on dishes coated with the anti-CD3 antibody as described in the Example and cultured in the presence of interleukin 2 for 5 days. The cultured cells were dedifferentiated to establish iPS cells (anti-CD3+IL2++ group). On the other hand, the mononuclear cells obtained from the peripheral blood were seeded on dishes uncoated with the anti-CD3 antibody and cultured using a KBM502 medium without interleukin 2 for 5 days to establish iPS cells (anti-CD3−IL2− group). The mononuclear cells were subjected to dedifferentiation by adding the Sendai virus that is able to express reprogramming factors to the mononuclear cells at MOI 3 for both of the anti-CD3+IL2+ group and the anti-CD3−IL2− group.

Figure 6:
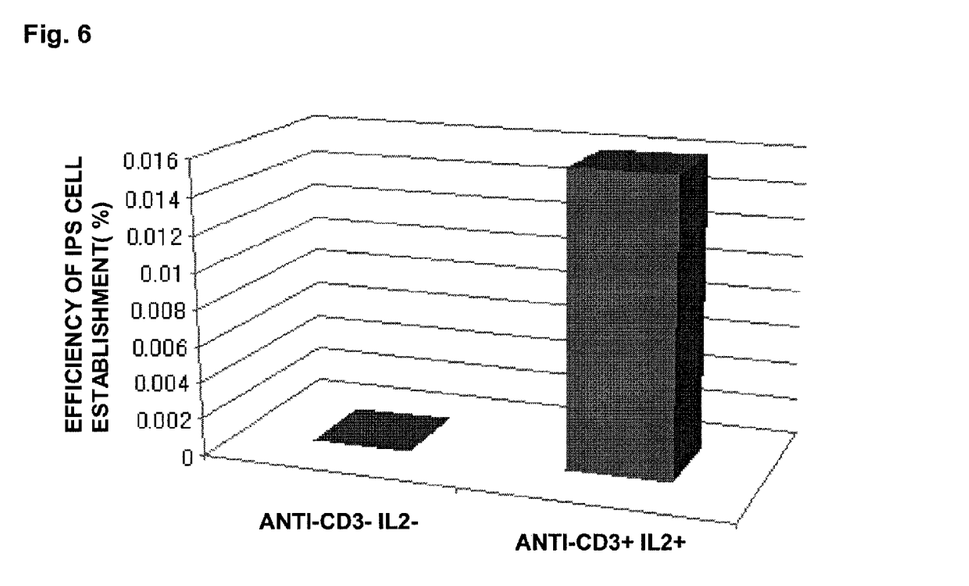
FIG. 6 shows a graph representing efficiencies of establishing iPS cells for two cases: when iPS cells were generated by culturing mononuclear cells in the presence of anti-CD3 antibody and interleukin 2 (anti-CD3+IL2+ group) and when iPS cells were generated by culturing mononuclear cells in the absence of anti-CD3 antibody and interleukin 2 (anti-CD3−IL2− group) in one Example of the present invention.

In the aforementioned establishment of the iPS cells, a ratio (%) of the number of mononuclear cells to which the Sendai virus was added to the number of alkaline phosphatase positive colonies was calculated as an efficiency of the iPS cell establishment. As shown in FIG. 6, the efficiency of the iPS cell establishment was 0% for the anti-CD3−IL2− group while 0.016% for the anti-CD3+IL2+ group.

As apparent from the above, the cells are required to be cultured in the presence of the anti-CD3 antibody and the interleukin 2 in order to generate the iPS cells from the mononuclear cells.

INDUSTRIAL APPLICABILITY

The present invention made it possible to produce iPS cells with high efficiency from mononuclear cells derived from peripheral blood.

The invention claimed is:

1. A method for producing a mammalian induced pluripotent stem cell comprising:
   (i) culturing a population consisting essentially of mammalian mononuclear cells isolated from peripheral blood for 3 to 14 days in the presence of anti-CD3 antibody and interleukin 2; and
   (ii) subjecting the cultured mononuclear cells to dedifferentiation by introduction of retroviral or Sendai viral vector(s) encoding Oct-4, Sox-2, Klf-4, and c-myc; and
   (iii) culturing the cells in (ii) under embryonic stem (ES) cell culture conditions to produce an induced pluripotent stem cell.

2. The method for producing a mammalian induced pluripotent stem cell according to claim 1, wherein:
   the recombinant expression vector is a Sendai virus vector.

3. The method for producing a mammalian induced pluripotent stem cell according to claim 1, wherein step (iii) comprises culturing the dedifferentiated mononuclear cells for 14 to 25 days in the presence of a growth factor.

4. The method for producing a mammalian induced pluripotent stem cell according to claim 1, wherein said peripheral blood is isolated from a human.

* * * * *